US007729763B2

(12) United States Patent
Kornet et al.

(10) Patent No.: US 7,729,763 B2
(45) Date of Patent: Jun. 1, 2010

(54) POST LONG PAUSE OVERDRIVE PACING IN RESPONSE TO ATRIAL TACHYARRYTHMIA EPISODE

(75) Inventors: Lilian Kornet, Maastricht (NL); Maurits Allessie, Maastricht (NL); Jaak M. O. Minten, Landen (BE)

(73) Assignee: Medtronic, Inc., Minneapolis, MN (US)

( * ) Notice: Subject to any disclaimer, the term of this patent is extended or adjusted under 35 U.S.C. 154(b) by 670 days.

(21) Appl. No.: 11/554,727

(22) Filed: Oct. 31, 2006

(65) Prior Publication Data

US 2007/0270910 A1 Nov. 22, 2007

Related U.S. Application Data

(60) Provisional application No. 60/747,627, filed on May 18, 2006.

(51) Int. Cl.
*A61N 1/362* (2006.01)
(52) U.S. Cl. .............................................. 607/14; 607/5
(58) Field of Classification Search .................... 607/14
See application file for complete search history.

(56) References Cited

U.S. PATENT DOCUMENTS

| 7,127,292 B2 | 10/2006 | Warman et al. | |
|---|---|---|---|
| 2003/0144698 A1* | 7/2003 | Ujhelyi et al. | 607/4 |
| 2004/0088010 A1* | 5/2004 | Warman et al. | 607/5 |
| 2004/0171959 A1* | 9/2004 | Stadler et al. | 600/518 |

OTHER PUBLICATIONS

"Advances in the treatment of atrial tachyarrhythmias: pacing, cardioversion, and defibrillation" by Carsten W. Israel, S. Serge Barold. Edition: illustrated Published by Wiley-Blackwell, 2002 ISBN 0879934972, 9780879934972. pp. 162-163 of 462.*
"Perioperative Care in Cardiac Anesthesia and Surgery" by C.H. Davy Cheng ISBN: 9780781757744. Published Nov. 15, 2005. p. 372.*
Purerfellner, Helmut, MD, et al: "Reduction of atrial tachyarrhythemia episodes during the overdrive pacing period using the post-mode switch overdrive pacing (PMOP) algorithm" Heart Rhythm, vol. 3, No. 10, Oct. 2006.

* cited by examiner

*Primary Examiner*—George R Evanisko
*Assistant Examiner*—Andrew Hayes
(74) *Attorney, Agent, or Firm*—Stephen W. Bauer

(57) ABSTRACT

This disclosure provides for methods and apparatus for preventing an early recurring atrial fibrillation and atrial flutter (AF) episode (herein "ERAF"). Some aspects of the foregoing involve commencing atrial overdrive pacing therapy delivery at an overdrive pacing rate upon detection of one of: (i) an AF episode and (ii) a relatively long pause between successive sensed P-waves during an AF episode. The AF episode typically has a cycle length interval of between about 100 ms and 300 ms, and the relatively long pause has a duration of between about 40 ms and 100 ms longer than the cycle length of the AF episode. Atrial overdrive pacing is delivered for a relatively short period of time after successful termination of the AF episode. Subsequently, the atrial pacing rate is rapidly decreased until either normal sinus rhythm or a lower programmed pacing rate is reached.

9 Claims, 4 Drawing Sheets

POST LONG PAUSE OVERDRIVE PACING IN RESPONSE TO ATRIAL TACHYARRYTHMIA EPISODE

CROSS REFERENCE TO RELATED APPLICATION

The present non-provisional U.S. patent application claims the benefit of prior provisional patent application having a common title which was filed on 18 May 2006 and is identified as application Ser. No. 60/747,627 the entire contents of said provisional application are hereby incorporated by reference herein, including all exhibits appended thereto.

FIELD OF THE INVENTION

The present invention relates to the field of diagnostics, monitoring and therapy delivery by implantable medical devices (IMDs) for patients experiencing atrial tachyarrhythmia episode, such as flutter, fibrillation, and the like.

BACKGROUND OF THE INVENTION

A representative previous invention includes U.S. patent application Ser. No. 10/284,873 to Warman et al. entitled, "Addressing Recurrent Atrial Fibrillation," the contents of which are incorporated herein by reference. As is know, some heart patients experience episodes of atrial tachyarrhythmia, including atrial fibrillation and/or atrial flutter (AF). Although AF episodes may not be immediately life-threatening, AF episodes may be associated with extreme symptoms, a reduced quality of life, and a reduced cardiac output. For heart patients having a multi-chamber pacemaker, AF episodes present an additional problem, in that the pacemaker may coordinate ventricular pacing with atrial activity. When an AF episode begins, it is undesirable for ventricular pacing to be timed according to atrial activity. Accordingly, some pacemakers are equipped with a "mode switching" capability. The principal purpose of such mode switching is to prevent the pacing system from delivering ventricular paces that track atrial activity when the atrium experiences an episode of atrial tachycardia. When the atrial rate is normal, the pacemaker assumes a tracking mode, such as DDD/DDDR, in which ventricular pacing tracks atrial activity. When an AF episode occurs, however, the pacemaker mode switches to a non-tracking mode, such as DDIR, and paces the ventricle independently of atrial activity.

When an AF episode occurs, the pacemaker or another medical device may apply therapy to terminate the AF episode. Therapy may comprise application of a cardioversion shock or administration of drug. Another therapy for atrial tachycardia is overdrive pacing of one or both atria, in which the pacemaker delivers pacing therapy at a rate faster than the then-present intrinsic rhythm. Overdrive pacing is often effective in disrupting an atrial arrhythmia such as AF and terminating the episode. Of course, an AF episode may also terminate spontaneously.

It has been observed that a recurring AF episode may occur within seconds or minutes after the termination of the first AF episode, and herein such an episode is referred to an early recurring AF (ERAF) condition. Although an ERAF episode does not always follow the termination of a preceding AF episode, it has been demonstrated clinically that a patient may have an increased risk of a recurrent AF episode for a period of time following a prior AF episode, both an initial and an ERAF episode. This phenomenon has been attributed to the fact that the local refractory period after AT is temporarily shortened, causing the substrate to be vulnerable to premature atrial beats which will re-induce AT/AF. In patients with AT/AF, who have a pacemaker implanted, atrial overdrive pacing may influence mechanisms which are held responsible for the early recurrence of AT/AF, including long pauses following premature beats, the number of premature beats, and the temporal dispersion of the refractory period. Some preliminary results have demonstrated a benefit of overdrive pacing. However, continuous overdrive pacing may not be well tolerated in the long term.

Therefore, with the Post-Mode Overdrive Pacing (PMOP) algorithm operational, overdrive pacing in the atrium is only activated in the phase shortly after a previous AF episode, when the tissue is vulnerable for premature beats to induce AT/AF. PMOP prevents AT/AF recurrence during the active phase of overdrive pacing. However, in this active phase only half of the AT/AF recurrences occur (31%), while half of the episodes are missed (29%) before PMOP is activated. The efficacy may be increased by preventing the episodes between device confirmed termination and before overdrive pacing is activated. Even more episodes can be prevented by overdrive pacing immediately when sinus rhythm occurs without waiting for device confirmed termination. Thus the clinical relevance of overdrive pacing could be improved theoretically at least a factor two. Based on the results of this study a new algorithm PLOP (Post-Long pause Overdrive Pacing) has been developed and tested in a clinical research study.

SUMMARY

The present invention relates to methods and apparatus for triggering delivery of atrial overdriving pacing therapy to prevent occurrences of ERAF. The invention involves delivering atrial overdrive pacing to the atria in a non-tracking pacing mode, upon detection of one of: (i) an AF episode and (ii) a relatively long pause between successive sensed P-waves during an AF episode, wherein the detection of the AF episode is characterized by an AF return cycle length (AFRCL) interval of between about 100 milliseconds (ms) and 360 ms, wherein the relatively long pause comprises an extended return cycle length (ERCL) length approximately at least 40 ms to 100 ms longer than the AFRCL, and wherein said overdrive pacing commences at a atrial pacing interval between the magnitude of the AFRCL and the ERCL, and then continuing said overdrive pacing therapy delivery for a period of time extending beyond successful termination of said AF episode and said relatively long pause and subsequently gradually decreasing the overdrive pacing rate until a normal sinus rhythm emerges.

Atrial tachycardia termination according to the invention can be triggered based upon a number of patient-specific programmable parameters such as amount (or number) ERAF episodes, frequency of ERAF episodes a patient has recently or historically endured, and the like. Also, the present termination techniques can be applied in lieu of or in addition to other related termination techniques such as PMOP. In one form of the invention a PMOP-type termination occurs following detection of an episode of atrial tachycardia (e.g., AF) and a PLOP-type termination attempt is undertaken following detection of the EF episode plus detection of a relatively long pause within said AF episode.

DETAILED DESCRIPTION OF THE ILLUSTRATED EMBODIMENTS

In the following detailed description, references are made to illustrative embodiments for the present invention which provides enhanced prevention of early recurring atrial fibrillation and flutter (ERAF) episodes to the benefit of subjects suffering from paroxysmal atrial arrhythmias.

Figure 1:
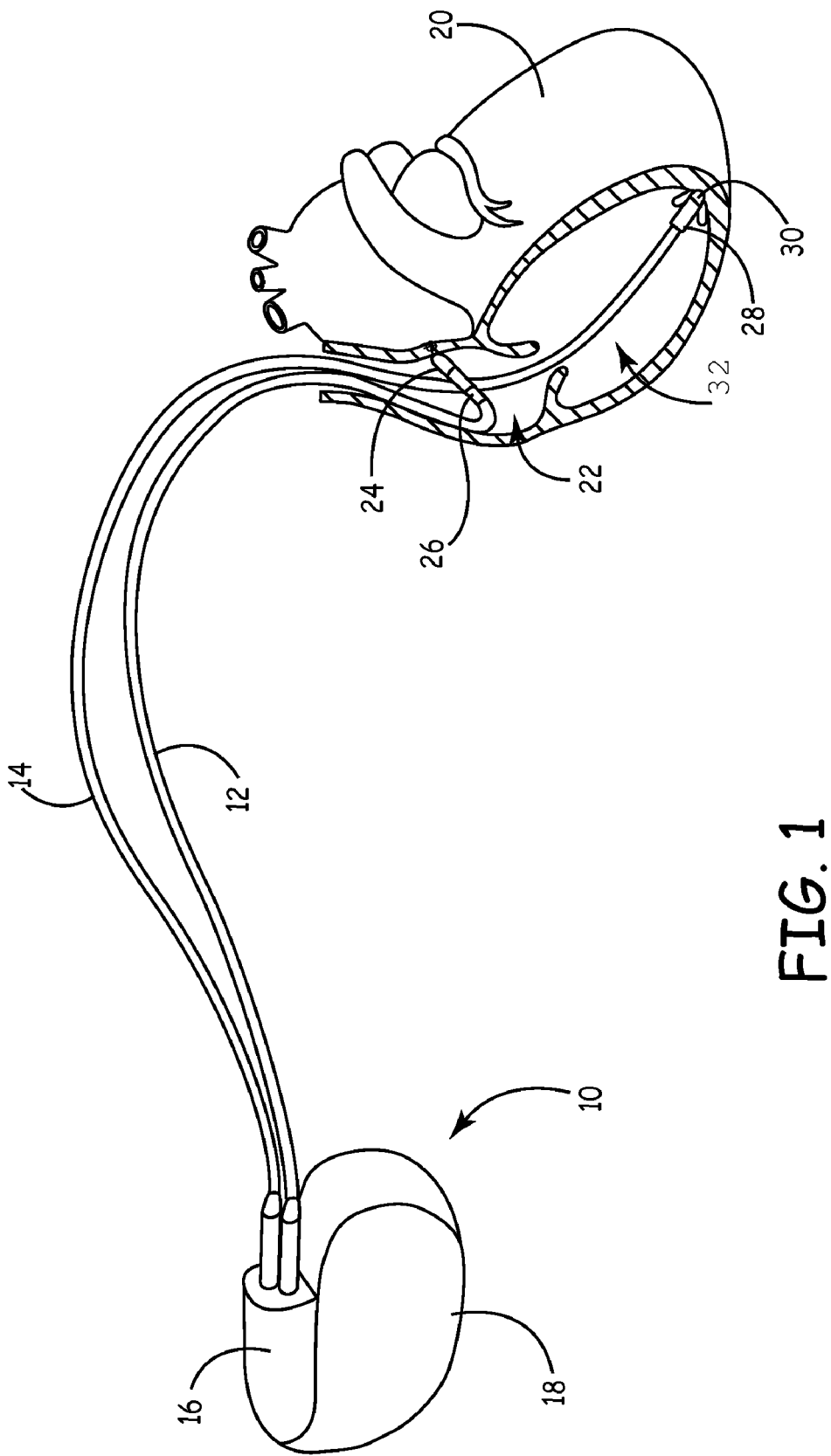
FIG. 1 is a schematic view of an exemplary implantable medical device that may practice the invention, with a heart.

FIG. 1 provides a schematic view of one embodiment of an IMD apparatus 10 that can be adapted to perform the methods according to the invention. IMD 10 can be configured to apply overdrive pacing to one or both atria following one of detection of an AF episode and a relatively long pause between successive P-waves in an effort to prevent an ERAF episode. In particular, IMD 10 can be programmed to, automatically respond to, or adjusted to deliver overdrive pacing therapy to prevent an ERAF episode. The IMD 10 comprises a pacemaker or cardioverter-defibrillator (ICD) comprising pacing and sensing leads 12,14 couple to a connector module 16 of a hermetically sealed enclosure 18 and are implanted near a heart 20 of a subject. Pacing and sensing leads 12,14 sense electrical signals attendant to the depolarization and repolarization of the heart 20, and further provide pacing pulses for causing depolarization of cardiac tissue in the vicinity of the distal ends of the leads.

Atrial pacing and sensing lead 12 extends from connector module 16 to the right atrium 22 of heart 20. At least one pair of atrial electrodes 24,26 are disposed in communication with an atrial chamber (e.g., as depicted, right atrium 22) at the distal end of atrial lead 12. Ventricular pacing and sensing lead 14 extends from connector module 16 to the right ventricle 32 of heart 20. Ventricular electrodes 28,30 are disposed in right ventricle 32 at the distal end of ventricular lead 14. Of course, the electrodes disposed to the leads 12,14 may be unipolar or bipolar electrodes and may comprise more than a pair of electrodes.

IMD 10 can delivery cardiac pacing therapy to a ventricle 32 via electrodes 28,30. IMD 10 can coordinate ventricular pacing with atrial activity sensed via atrial electrodes 24,26. Atrial electrodes 24,26 can also be employed to sense an atrial tachyarrhythmia such as fibrillation or flutter (AF), and to administer therapy, such as overdrive pacing. IMD 10 switch pacing modes upon detection of AF.

Overdrive pacing administered via atrial electrodes 24,26 has been shown to terminate an AF episode in progress and can prevent an AF episode from recurring. The present invention is directed to triggering overdrive pacing therapy delivery to terminate the AF episode or to prevent an ERAF episode parameters that will give IMD 10 a good chance to prevent a recurrent AF episode with overdrive pacing therapy. In particular, IMD 10 may regulate the rate and duration of overdrive pacing and may regulate other facets of overdrive pacing as well.

Figure 2:
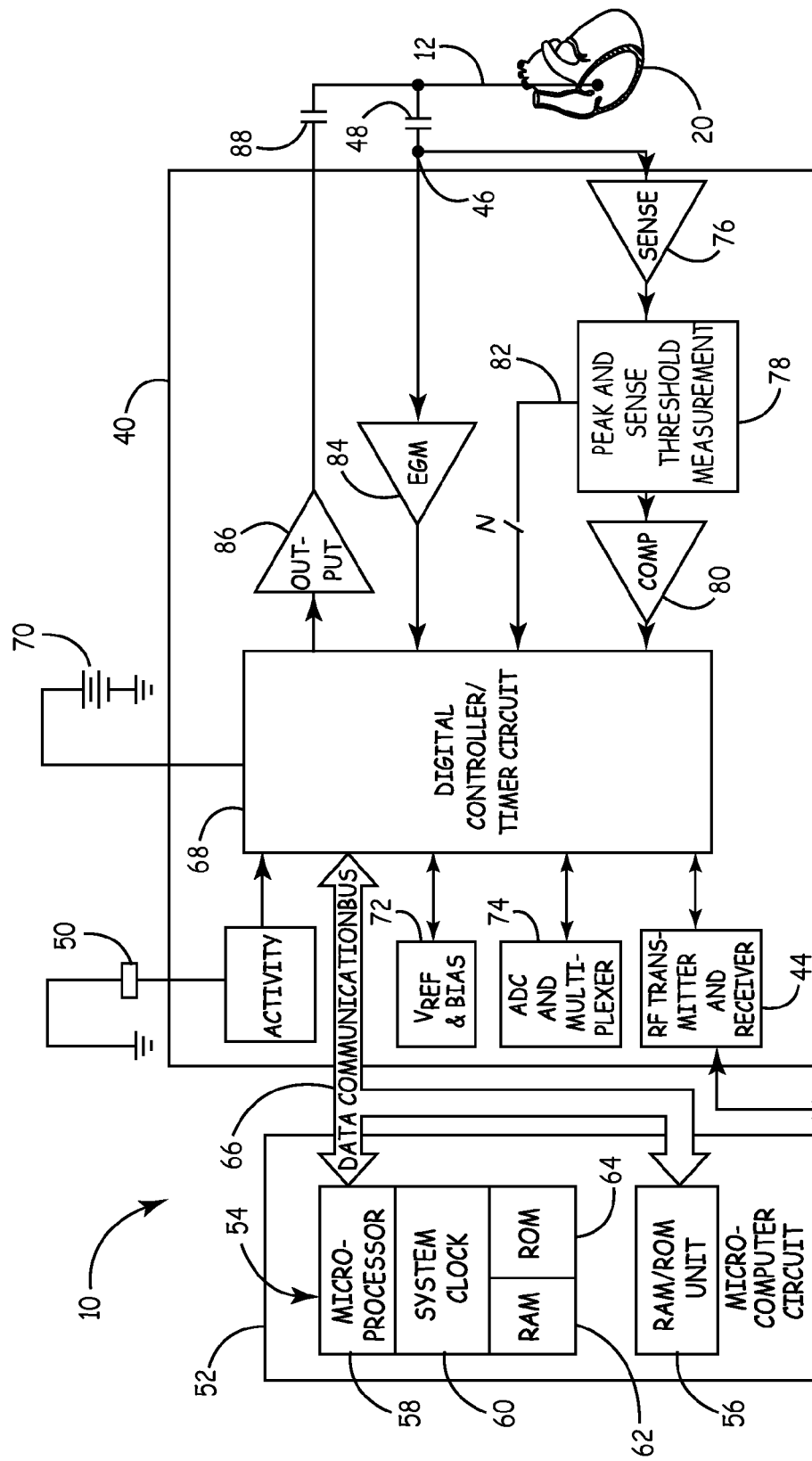
FIG. 2 is a block diagram illustrating the constituent components of an implantable medical device such as the implantable medical device in FIG. 1.

FIG. 2 shows a block diagram illustrating the constituent components of an exemplary IMD 10 in accordance with one embodiment of the invention, in which IMD 10 is a pacemaker having a microprocessor-based architecture. IMD 10 is programmable and may be programmed with an external programming unit (not shown in the figures). The programmer may provide a series of encoded signals to IMD 10 via wireless telemetry. An input/output circuit 40 may be coupled to an antenna 42 to permit uplink/downlink telemetry through an RF transmitter and receiver telemetry unit 44. In addition to transmitting or receiving programming instructions, telemetry unit 44 may transmit or receive information. Transmitted and received information may include, for example, instructions that cause a processor (such as microprocessor 58, described below) to practice the techniques of the invention. Transmitted and received information may also include default overdrive pacing parameters, one or more overdrive pacing thresholds as described below, historical data concerning AF episodes collected by IMD 10 and/or the number and/or length of the temporal pauses used to trigger overdrive pacing. Any of a number of programming and telemetry methodologies may be employed to transmit information to and receive information from IMD 10.

Atrial lead 12 and ventricular lead 14 (not shown in FIG. 2) are coupled to input/output circuit 40. For simplicity, IMD 10 in FIG. 2 is shown with atrial lead 12 connected thereto, but similar circuitry and connections not explicitly shown in FIG. 2 may apply to ventricular lead 14. Lead 12 is coupled to node 46 in IMD 10 through input capacitor 48. Input/output circuit 40 may also deliver pacing stimuli to the atrium as will be described in more detail below.

Input/output circuit 40 may further receive input from an activity sensor or accelerometer 50, such as a piezoceramic accelerometer bonded to a hybrid circuit located inside enclosure 18 (shown in FIG. 1). Activity sensor 50 typically (although not necessarily) provides a sensor output that varies as a function of a measured parameter relating to a patient's metabolic requirements.

IMD 10 includes a microcomputer circuit 52. Microcomputer circuit 52 stores and executes software-implemented algorithms for detecting and responding to arrhythmias such as AF. In some embodiments of the invention, IMD 10 may be programmed to operate in various rate-responsive or non-rate-responsive modes. In addition, microcomputer circuit 52 may store and execute software-implemented algorithms for managing overdrive pacing parameters according to the techniques of the invention, and for controlling delivery of overdrive pacing therapy according to the overdrive pacing parameters.

Microcomputer circuit 52 may include an on-board circuit 54 and off-board circuit 56. On-board circuit 54 includes microprocessor 58, system clock circuit 60 and on-board random-access memory (RAM) 62 and read-only memory (ROM) 64. Off-board circuit 56 comprises a RAM/ROM unit. On-board circuit 54 and off-board circuit 56 are each coupled by a data communication bus 66 to digital controller/timer circuit 68. Microcomputer circuit 52 may comprise a custom integrated circuit device augmented by standard RAM/ROM components. Memory 56, 62 or 64 may store overdrive pacing parameters, and may store data pertaining to the evaluation and efficacy of overdrive pacing therapy, as will be described below. Other information may of course be stored such as counter or data relating to PLOP criteria met, PLOP deactivated by an on-going episode of atrial tachycardia, PLOP deactivated due to a newly-detected atrial tachycardia and the like.

Electrical components shown in FIG. 2 are powered by an implantable battery power source 70. For the sake of clarity, the coupling of battery power source 70 to the various components of IMD 10 is not shown in the FIG. 2. VREF and bias circuit 72 generates stable voltage reference and bias currents for analog circuits included in input/output circuit 40. Analog-to-digital converter (ADC) and multiplexer unit 74 digitizes analog signals and voltages for digital processing.

Operating commands for controlling the timing of electrical stimulations delivered to heart 20 by IMD 10 are coupled from microprocessor 58 via data bus 66 to digital controller/timer circuit 68, where digital timers and counters establish the various refractory, blanking and other timing windows used in the detection of cardiac activity and the delivery of electrical stimulations.

Sensing circuitry coupled to digital controller/timer circuit 68 detects cardiac activity. Cardiac signals detected via lead 12 are processed by sensing circuitry, which includes sense amplifier 76, peak sense and threshold measurement unit 78 and comparator/threshold detector 80. In general, sense amplifier 76, peak sense and threshold measurement unit 78 and comparator/threshold detector 80 cooperate to sense the occurrence and timing of cardiac events such as atrial activations. Sense amplifier 76 amplifies sensed electrical cardiac signals and provides an amplified signal to peak sense and threshold measurement unit 78, which in turn provides an indication of peak sensed voltages and measured sense amplifier threshold voltages on multiple conductor signal path 82 to digital controller/timer circuit 68. An amplified sense amplifier signal is also provided to comparator/threshold detector 80.

Cardiac signals detected via lead 12 may also be received by electrogram (EGM) amplifier 84. In general, the electrogram signal supplied by EGM amplifier 84 preserves the morphology of the cardiac signal. Digital controller/timer circuit 68 may process the electrogram signal supplied by EGM amplifier 84, and may transmit the electrogram signal to an external programmer for observation and analysis by a physician.

Output pulse generator 86 provides amplified pacing stimuli to heart 20 through coupling capacitor 88 in response to a pacing trigger signal provided by digital controller/timer circuit 68. The conditions that trigger generation of a pacing trigger signal may vary from patient to patient, and the conditions that may trigger generation of an atrial pacing trigger signal need not be the same as the conditions that trigger generation of a ventricular pacing trigger signal. In an embodiment of the invention, digital controller/timer circuit 68 generates atrial pacing trigger signals that cause overdrive pacing of the atrium to terminate an AF episode or to prevent a recurrent AF episode from occurring.

The invention is not limited to application with IMD 10 as depicted in FIGS. 1 and 2. The techniques of the invention may be practiced by, for example, single-chamber pacemakers, or double-, triple- or quadruple-chamber pacemakers. The invention may be practiced by devices that provide a variety of pacing, cardioversion and defibrillation therapies.

Devices that perform overdrive pacing of the atrium supply pacing stimuli to the atrium at a rate, called the "overdrive rate." The overdrive rate may be expressed as the number of paces supplied per unit time during overdrive pacing. In addition, devices that perform overdrive pacing of the atrium supply pacing stimuli at the overdrive rate for a duration of time, called the "overdrive duration." The overdrive rate (relative to a then-current sinus rhythm or paced rate) and overdrive duration are two significant overdrive pacing parameters, but not the only parameters pertaining to overdrive pacing. Other overdrive pacing parameters will be described below.

Figure 3:
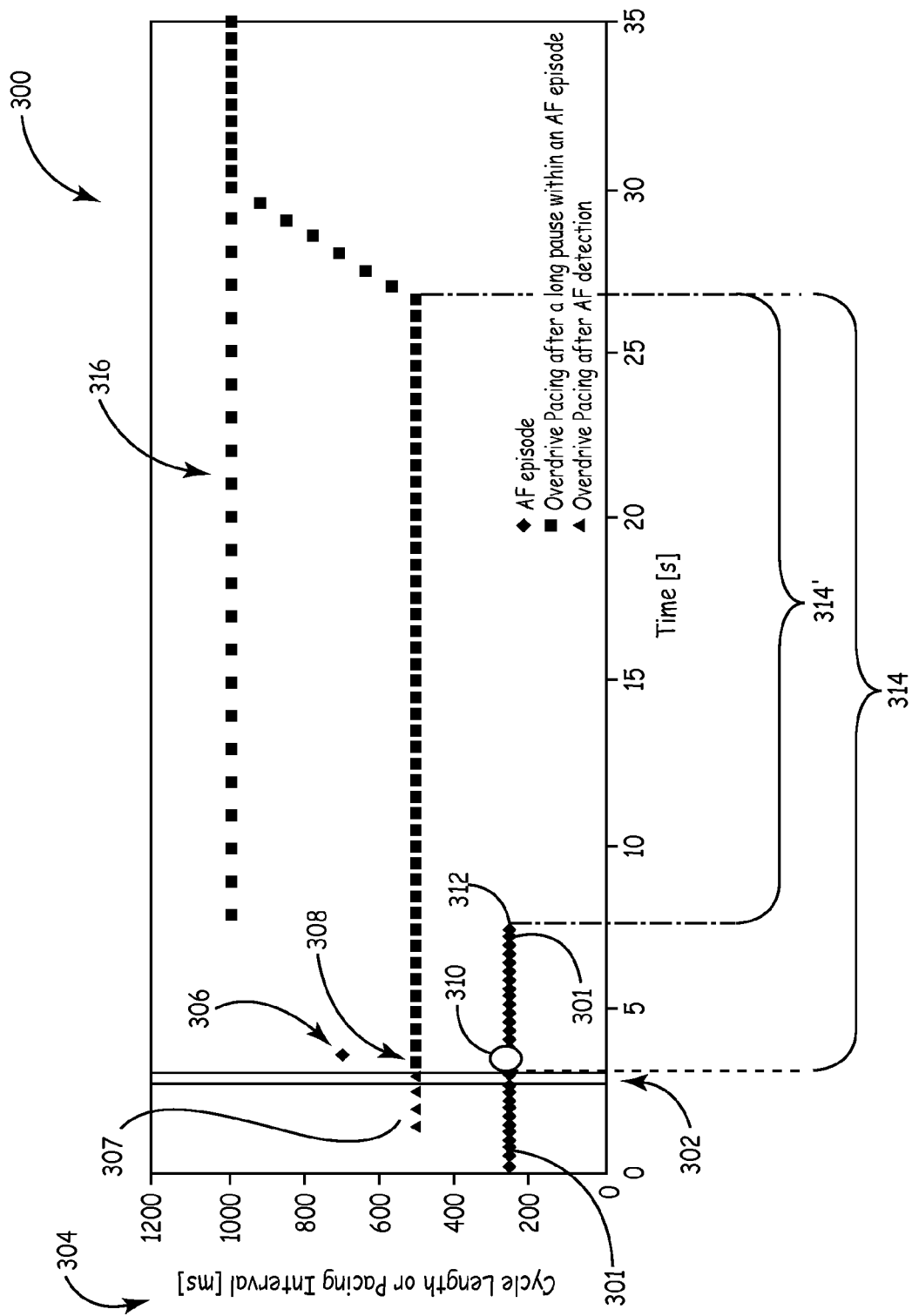
FIG. 3 is a temporal plot of an exemplary application of the techniques of the invention in which during a period of approximately 35 seconds ERAF is prevented.

FIG. 3 is a timing diagram 300 illustrating an illustrative embodiment of overdrive pacing parameters and management of the parameters according to certain aspects of the invention. The timing diagram 300 illustrates an AF episode 301 of atrial beats characterized by a collection of rapid intrinsic beats (denoted by diamond-shaped symbols) having a cycle length interval 304 (when referring to intrinsic activity such as the AF episode 301) of approximately 250 ms (equal to 240 beats per minute, bpm) beginning at time zero (0) and continuing essentially uninterrupted for approximately three seconds (at 302).

According to the invention, initial delivery of atrial overdrive pacing (denoted as triangle-shaped symbols 307 having a overdrive pacing interval of approximately 500 ms or 120 pacing-pulses per minute, ppm) commences almost immediately (at approximately one or two seconds into the AF episode 301) and in contrast to known overdrive AF termination techniques continues for a relatively short period of time denoted by reference numeral 314 (e.g., which as depicted is approximately 20 seconds) following termination of the AF episode 301 (at time 312). One aspect of the present invention relates to the fact that upon expiration of the relatively short period of time 314 during which overdrive pacing 308 is delivered the pacing rate, or interval 304, rapidly increases (e.g., within approximately three seconds) to the emergent intrinsic rate (1000 ms cycle length or 60 bpm) which is denoted by round-shaped symbols 316.

Thus, according to the invention the atrial overdrive pacing (denoted as square-shaped symbols having a pacing interval 304 of approximately 500 ms or 120 ppm) continues at a time 308 more or less immediately following a relatively long pause 306 in the AF episode 301 which, as depicted, is a atrial contraction having a cycle length of approximately 700 ms. The AF episode 301 shown in FIG. 3 then resumes at approximately its prior return cycle length 304 (250 ms or 240 bpm) following what herein is referred to as a long pause (denoted as circle-shaped symbol 310) during which time the overdrive atrial pacing 308 continues to be delivered at an overdrive pacing interval of approximately 500 ms. The example depicted in FIG. 3 thus illustrates a technique for both terminating an AF episode and preventing a ERAF episode within a time span on the order of one-half of a minute during which the an AF rate of about 240 bpm is converted back to normal sinus rhythm of about 60 bpm.

Figure 4:
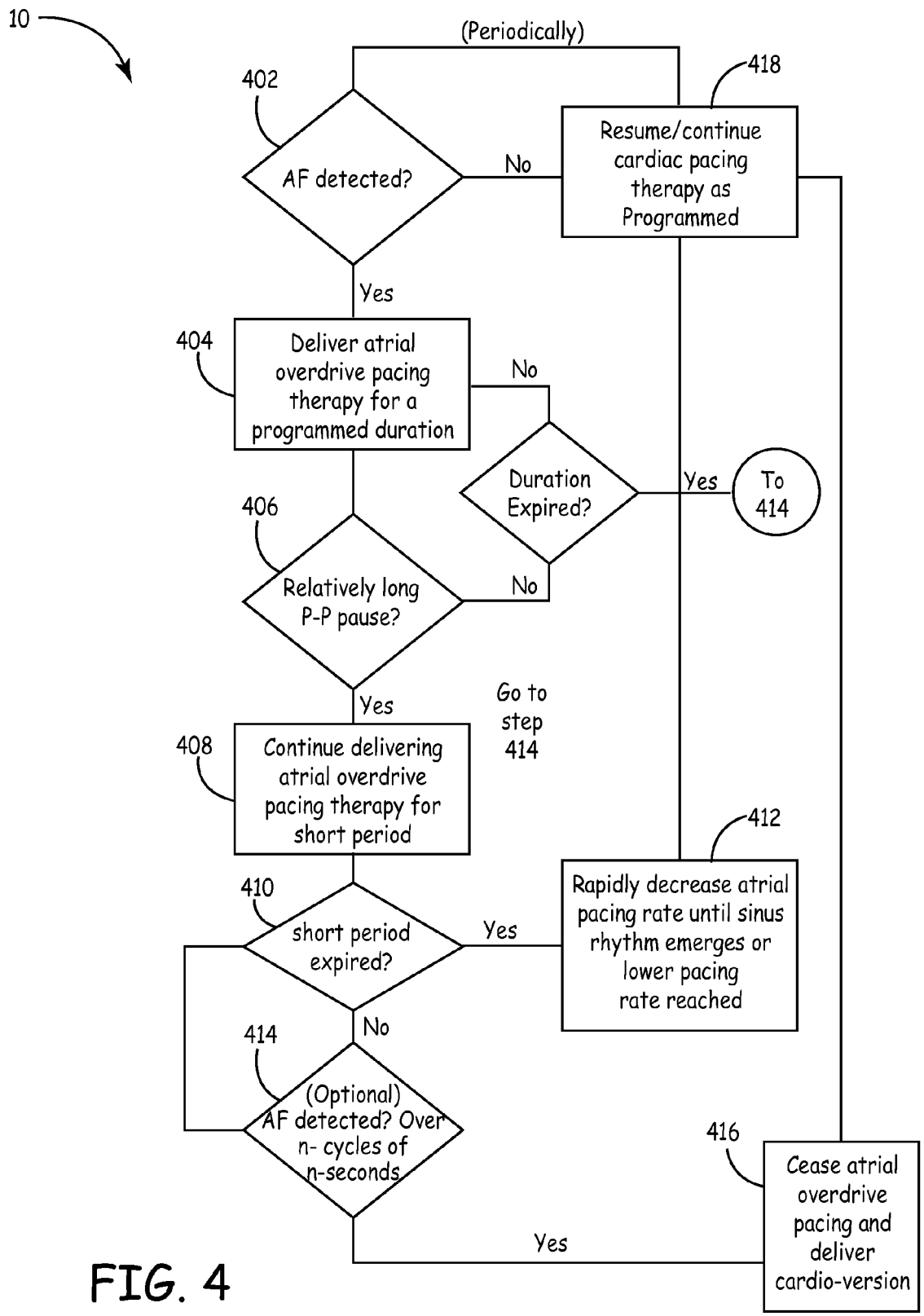
FIG. 4 is a simple flow chart depicting one embodiment of a method according to the invention wherein an AF episode is detected at and overdrive pacing is activated for a programmed duration to prevent ERAF.

Referring now to FIG. 4, a simple flow chart depicts one embodiment of a method 400 according to the invention wherein an AF episode is detected at 402 and overdrive pacing is activated at 404 for a programmed duration. At 406 a sensor disposed in communication with one or both atria is operatively implemented to detect the amount of time elapsed between successive atrial depolarizations (P-waves) that includes criteria for determining when a relatively long pause between said successive P-waves occurs. In the event that such a long pause is detected the process 400 proceeds to step 408 wherein the atrial overdrive pacing therapy is delivered for a short period of time (e.g., on the order of about 20 to about approximately 60 seconds). In the event that no relatively long pause is detected at 406 the process 400 proceeds to decision step 405 to determine if the programmed duration has expired. If it has the method 400 proceeds to decision step 414 (as depicted). If the duration has not expired the method 400 continues to deliver atrial overdrive pacing at 404 for the remainder of the programmed duration. In the event that a relatively long pause is detected at 406 the method 400 proceeds to step 408 wherein atrial overdrive pacing therapy is delivered for a programmable short period of time (e.g., 20 to about 60 seconds). If the programmable short period of time has expired the method 400 proceeds to step 412 and the atrial pacing rate is rapidly decreased until either normal sinus rhythm emerges or a programmed lower pacing rate is reached and the method 400 proceeds to step 418 wherein a previously programmed chronic pacing regimen resumes or, as applicable, continues to be delivered. In the event that the programmable short period of time has not expired the method 400 optionally proceeds to decision step 414 wherein detection of AF is attempted (over several cardiac cycles or from n-seconds, etc.). If no AF is detected this optional aspect of method 400 reverts to decision step 410 to determine if the short period has expired. If the short period has expired, as before, the method 400 proceeds to step 412, or optionally, to step 414. In the event that AF is detected at decision step 414 the method 400 proceeds to step 416 and atrial overdrive pacing ceases and delivery of cardioversion therapy occurs. The method 400 then proceeds to step 418 with periodic, or continuous reference to decision step 402 thereafter.

Certain prior art techniques involve detecting termination of an AF episode and then waiting a period of time before applying overdrive pacing therapy wherein a pacemaker employs an algorithm for sensing termination of an AF episode. The pacemaker may sense a set number of normal sinus rhythm beats, for example, to confirm that the AF episode has terminated. In other prior art techniques, the pacemaker does not employ a waiting period. The pacemaker simply delivers a cardioversion shock intended to terminate the AF episode, and subsequently begins delivery of overdrive pacing after delivering the shock. However, in all these prior art techniques the inventors have noticed that following termination of an AF episode, the patient is at risk of experiencing a recurrent AF episode. However, various definitions of recurrent can be found among clinicians and physicians. For example, one may deem that an AF episode is "recurrent" when the episode follows within a minute of an earlier terminated episode of AF. Another physician may deem that an AF episode is "recurrent" when the episode follows within three hundred beats of an earlier terminated AF episode. A third physician may use "recurrent" to refer to an AF episode that follows within ten minutes or six hundred beats of an earlier terminated episode, whichever is longer.

In contrast, the present invention encompasses all such usages of the term "recurrent" albeit somewhat redefined herein as "early recurrent" (or ERAF). As a result, when the patient is at risk of experiencing an ERAF episode, a pacemaker begins overdrive pacing by delivering a pacing stimulus prior to a scheduled stimulus delivery, thereby overdriving the atrium as described and depicted hereinabove.

In prior art techniques, the pacemaker typically does not abruptly switch to an overdrive pacing rate but rather gradually ramps to a programmed overdrive pacing rate over a transition interval wherein the rate is incrementally increased to the overdrive pacing rate. It should be noted that in prior art techniques and according to certain embodiments of the invention, a pacemaker can delivery pacing therapy to one or both atria at an overdrive pacing rate.

Therefore, in accordance with the present invention, diverse methods and apparatus are provided for preventing ERAF events or episodes to thereby reduce the AF burden of patients suffering from AF. That is, the invention is directed to techniques by which a pacemaker responds to detection of an AF episode and provides overdrive pacing for a short duration timed from detection of a relatively long pause occurring within the AF episode.

Other related techniques and modifications of the foregoing can be appreciated following review of this patent disclosure. For example, if a programmable amount or number of ERAF events occur one and/or both therapies or atrial termination algorithms can be activated; namely a first in which overdrive pacing is applied after AF detection and a second wherein overdrive pacing is started following AF detection and detection of a long pause. In addition, the PLOP algorithm can be triggered based at least in part upon the amount (or number) of ERAF episodes detected, the frequency, the percentage that recur and the like, so that the PLOP algorithm is activated only when particularly relevant. We found that no effect on burden could be detected for PMOP 90 bpm.

In addition, it will be understood that specifically described structures, functions and operations set forth in the above-referenced patents can be practiced in conjunction with the present invention, but they are not essential to its practice. It is therefore to be understood, that within the scope of the appended claims, the invention may be practiced otherwise than as specifically described without actually departing from the spirit and scope of the present invention.

The invention claimed is:

1. A method of preventing an early recurring atrial fibrillation or flutter (AF) episode, comprising:
   detecting an AF episode;
   commencing atrial overdrive pacing therapy delivery at an overdrive pacing rate upon detection of a relatively long pause between successive sensed P-waves during the detected AF episode,
      wherein detecting the AF episode is characterized by detecting an AF return cycle length (AFRCL) interval of between about 100 milliseconds (ms) and about 360 ms,
      wherein the relatively long pause comprises an extended return cycle length (ERCL) length approximately 40 ms to 100 ms longer than the AFRCL, and
      wherein said overdrive pacing therapy commences at a atrial pacing interval having a duration between the AFRCL and the ERCL; and
   continuing said overdrive pacing therapy delivery for a relatively short period of time extending beyond successful termination of said AF episode; and
   rapidly decreasing the overdrive pacing rate until one of a normal sinus rhythm emerges and a lower programmed pacing rate is reached.

2. A method according to claim 1, wherein the relatively short period of time comprises a period of time having a duration of between a few seconds and about 30 minutes.

3. A method according to claim 1, wherein the relatively short period of time comprises a programmable interval and said interval begins at about one minute and ends at less than about 60 minutes.

4. A method according to claim 1, wherein the relatively short period of time comprises a programmable interval of between about 20 seconds and several minutes.

5. A method according to claim 1, wherein rapidly decreasing the overdrive pacing rate comprises reducing the rate by increasing pacing intervals in successive steps by between about 10 milliseconds (ms) and about 20 ms.

6. A method according to claim 5, wherein rapidly decreasing the overdrive pacing rate comprises reducing the rate in successive steps wherein each step comprises between one and ten cardiac cycles.

7. A method according to claim 1, wherein rapidly decreasing the overdrive pacing rate comprises reducing the rate within less than about twenty cardiac cycles.

8. A method according to claim 1, wherein rapidly decreasing the overdrive pacing rate comprises reducing the rate within less than about thirty cardiac cycles.

9. A method according to claim 1, wherein commencing atrial overdrive pacing therapy delivery at an overdrive pacing rate comprises delivering the therapy via one of:
   a least one epicardial patch-type electrode,
   at least one electrode adapted to be disposed within an atrial chamber,
   at least one electrode adapted to be disposed within a portion of a cardiac vein.

* * * * *